(12) United States Patent
Stenlund

(10) Patent No.: US 11,887,459 B2
(45) Date of Patent: *Jan. 30, 2024

(54) WEARABLE DEVICE WITH MULTIBIOMETRY

(71) Applicant: ASSA ABLOY AB, Stockholm (SE)

(72) Inventor: Peter Stenlund, Stockholm (SE)

(73) Assignee: ASSA ABLOY AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/101,874

(22) Filed: Jan. 26, 2023

(65) Prior Publication Data

US 2023/0162585 A1    May 25, 2023

Related U.S. Application Data

(63) Continuation of application No. 17/510,129, filed on Oct. 25, 2021, now Pat. No. 11,600,160, which is a
(Continued)

(30) Foreign Application Priority Data

Oct. 24, 2017    (EP) .................................. 17198077

(51) Int. Cl.
*G08B 21/04*    (2006.01)
*A61B 5/026*    (2006.01)
(Continued)

(52) U.S. Cl.
CPC .......... *G08B 21/0446* (2013.01); *A61B 5/026* (2013.01); *B60R 25/01* (2013.01); *G06F 17/142* (2013.01); *A61B 2503/22* (2013.01)

(58) Field of Classification Search
CPC ...... G08B 21/0446; A61B 5/026; B60R 25/01
See application file for complete search history.

(56) References Cited

U.S. PATENT DOCUMENTS 6,571,193 B1    5/2003 Unuma et al.
9,762,581 B1    9/2017 Wang et al.
(Continued)

FOREIGN PATENT DOCUMENTS

EP          2335231         12/2012
KR   10-2017-0112778        10/2017
WO        2019081467          5/2019

OTHER PUBLICATIONS

Extended Search Report for European Patent Application No. 17198077.4, dated Nov. 29, 2017, 6 pages.
(Continued)

*Primary Examiner* — Curtis B Odom
(74) *Attorney, Agent, or Firm* — Schwegman Lundberg & Woessner, P.A.

(57) ABSTRACT

It is provided a wearable device for determining when a user has fallen down. The wearable device comprises: a first biometric sensor for obtaining first biometric data of the user, wherein the first biometric sensor is a first accelerometer configured to measure acceleration of a part of a first limb of the user; a second biometric sensor for obtaining second biometric data of the user comprising a finger pressure parameter; and a third biometric sensor for obtaining third biometric data, the third biometric sensor being a second accelerometer configured to measure acceleration of a body part of the user being distinct from the first limb. The wearable device is configured to determine an identity of the user is based on the first biometric data, the second biometric data and the third biometric data, the identity being used to control access to a physical space, and to determine when the user has fallen down.

13 Claims, 2 Drawing Sheets

Related U.S. Application Data continuation of application No. 16/756,747, filed as application No. PCT/EP2018/078967 on Oct. 23, 2018, now Pat. No. 11,189,149.

(51) Int. Cl.
*B60R 25/01* (2013.01)
*G06F 17/14* (2006.01)

(56) References Cited

U.S. PATENT DOCUMENTS

| | | | |
|---|---|---|---|
| 11,189,149 B2* | 11/2021 | Stenlund | G06F 21/35 |
| 11,600,160 B2 | 3/2023 | Stenlund | |
| 2014/0085050 A1 | 3/2014 | Luna | |
| 2014/0143064 A1 | 5/2014 | Tran | |
| 2016/0143546 A1 | 5/2016 | McCombie et al. | |
| 2017/0032114 A1 | 2/2017 | Turgeman | |
| 2021/0192920 A1 | 6/2021 | Stenlund | |
| 2022/0044540 A1 | 2/2022 | Stenlund | |

OTHER PUBLICATIONS

International Search Report and Written Opinion for International (PCT) Patent Application No. PCT/EP2018/078967, dated Nov. 16, 2018, 11 pages.

International Preliminary Report on Patentability for International (PCT) Patent Application No. PCT/EP2018/078967, dated Nov. 28, 2019, 13 pages.

Official Action with English Translation for Korea Patent Application No. 10-2020-7011030, dated Aug. 26, 2021, 15 pages.

Official Action for U.S. Appl. No. 16/756,747, dated Apr. 9, 2021 6 pages.

Notice of Allowance for U.S. Appl. No. 16/756,747, dated Jul. 22, 2021 7 pages.

Notice of Allowance for U.S. Appl. No. 17/510,129, dated Oct. 27, 2022 7 pages.

"U.S. Appl. No. 16/756,747, Preliminary Amendment filed Apr. 16, 2020", 6 pgs.

"U.S. Appl. No. 16/756,747, Response filed Jul. 8, 2021 to Non Final Office Action dated Apr. 9, 2021", 6 pgs.

"U.S. Appl. No. 16/756,747, Notice of Allowance dated Nov. 5, 2021", 2 pgs.

"U.S. Appl. No. 17/510,129, 312 Amendment filed Jan. 26, 2023", 3 pgs.

"U.S. Appl. No. 17/510,129, PTO Response to Rule 312 Communication dated Feb. 7, 2023", 2 pgs.

* cited by examiner

WEARABLE DEVICE WITH MULTIBIOMETRY

CROSS REFERENCE TO RELATED APPLICATIONS

This application is a continuation of U.S. patent application Ser. No. 17/510,129, filed Oct. 25, 2021, which is a continuation of U.S. patent application Ser. No. 16/756,747, filed Apr. 16, 2020, now U.S. Pat. No. 11,189,149, issued Nov. 30, 2021, which is a national stage application under 35 U.S.C. 371 and claims the benefit of PCT Application No. PCT/EP2018/078967 having an international filing date of Oct. 23, 2018, which designated the United States, which PCT application claimed the benefit of European Patent Application No. 17198077.4 filed Oct. 24, 2017, the disclosure of each of which are incorporated herein by reference.

TECHNICAL FIELD

The invention relates to identification of a user using a wearable device.

BACKGROUND

With online shopping steadily increasing, deliveries of physical goods are also increasing. Consumers want fast and cheap delivery, and the delivery companies want efficiency and safety for their deliveries. However, thefts from delivery vehicles and attacks against drivers are increasing since the value of the goods increases.

Current security solutions for delivery vehicles rely on traditional vehicle locks or even padlocks. Moreover, there are no satisfactory security solutions for drivers of delivery vehicles.

SUMMARY

It is an object to improve security for drivers of cargo vehicles.

According to a first aspect, it is provided a wearable device for determining when a user has fallen down. The wearable device comprises: a first biometric sensor for obtaining first biometric data of the user, wherein the first biometric sensor is a first accelerometer configured to measure acceleration of a part of a first limb of the user; a second biometric sensor for obtaining second biometric data of the user comprising a finger pressure parameter; and a third biometric sensor for obtaining third biometric data, the third biometric sensor being a second accelerometer configured to measure acceleration of a body part of the user being distinct from the first limb of the user. The wearable device is configured to determine an identity of the user is based on the first biometric data, the second biometric data and the third biometric data, the identity being used to control access to a physical space, and to determine when the user has fallen down based on the first biometric data and the third biometric data.

The first biometric sensor may comprise a fingerprint sensor.

The first biometric sensor may comprise a blood flow sensor.

The first biometric sensor may comprise a gyro.

The physical space may form part of a vehicle.

According to a second aspect, it is provided a method for determining when a user has fallen down. The method is performed in a wearable device and comprising the steps of: obtaining first biometric data of the user using a first biometric sensor of the wearable device, wherein the first biometric sensor is a first accelerometer configured to measure acceleration of a part of a first limb of the user; obtaining second biometric data of the user using a second biometric sensor of the wearable device, the second biometric data comprising a finger pressure parameter; obtaining third biometric data of the user using a third biometric sensor of the wearable device, wherein the third biometric sensor is a second accelerometer configured to measure acceleration of a body part of the user being distinct from the first limb of the user; determining an identity of the user based on the first biometric data and the second biometric data; and determining when the user has fallen down based on the first biometric data and the third biometric data.

According to a third aspect, it is provided a computer program for determining when a user has fallen down. The computer program comprising computer program code which, when run on a wearable device causes the wearable device to: obtain first biometric data using a first biometric sensor of the wearable device, wherein the first biometric sensor is a first accelerometer configured to measure acceleration of a part of a first limb of the user; obtain second biometric data using a second biometric sensor of the wearable device, the second biometric data comprising a finger pressure parameter; obtain third biometric data of the user using a third biometric sensor of the wearable device, wherein the third biometric sensor is a second accelerometer configured to measure acceleration of a body part of the user being distinct from the first limb of the user; determine an identity of the user based on the first biometric data and the second biometric data and determine when the user has fallen down based on the first biometric data and the third biometric data.

According to a fourth aspect, it is provided a computer program product comprising a computer program according to the third aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which.

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

Figure 1:
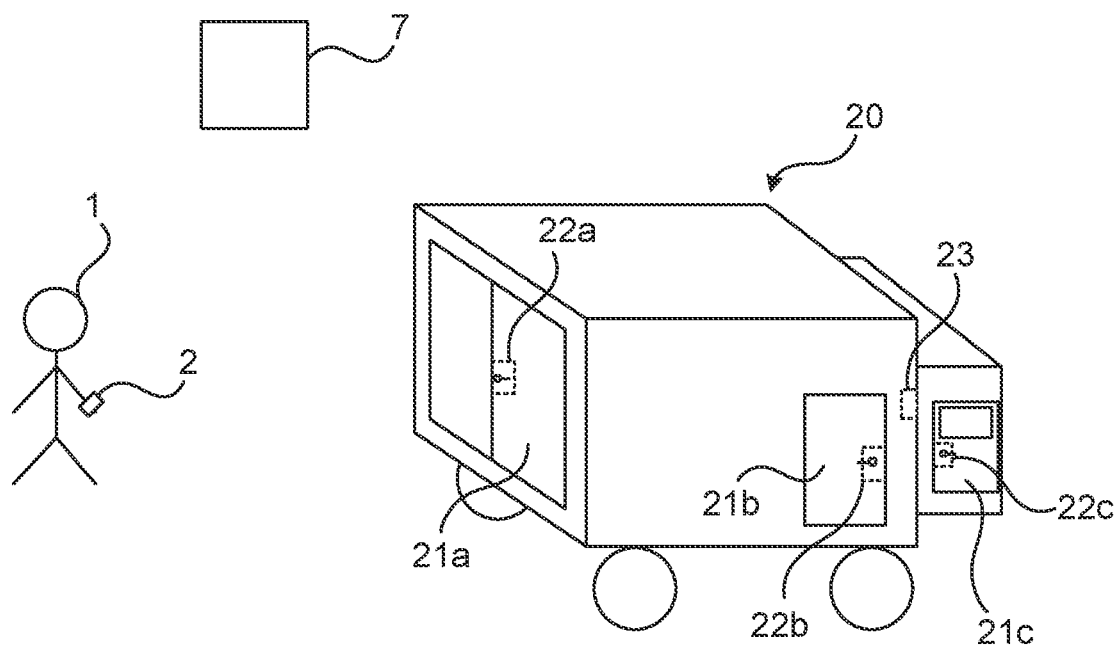
FIG. 1 is a schematic diagram illustrating an environment in which embodiments presented herein can be applied.

FIG. 1 is a schematic diagram illustrating an environment in which embodiments presented herein can be applied.

A user 1 is a logistics person associated with a vehicle 20, for instance the currently assigned driver of the vehicle. The vehicle 20 is suitable for carrying cargo and can be a van, a lorry, a car, etc. The cargo can be loaded in the vehicle 20 e.g. in the form of boxes, optionally on pallets.

The vehicle 20 is provided with a back door 21a and one or more cabin doors 21c (only one seen in FIG. 1). The function of the back door 21a can equally well be performed by a tail lift and/or roller shutter. Optionally, a side door 21b for access to the cargo area of the vehicle is provided.

The back door 21a is secured by a first electronic lock 22a, the cabin door(s) 21c are secured by a third electronic lock 22c and the optional side door 21b is secured by an optional second electronic lock 22b. Optionally, an electronic access control device 23 controls access to operation of the vehicle, corresponding to an ignition key.

The user 1 carries a wearable device 2. A wearable device is an electronic device which can be worn by the user. For instance the wearable device can be in the form of a wristband or watch. As explained in more detail below, the wearable device 2 is used to identify the user 1 using at least two biometric sensors.

The user 1 can request access to a physical space by placing the wearable device 2 in close proximity (e.g. centimetres) or in contact with a tag (not shown) associated with the electronic lock securing the physical space in question. The communication between the tag and the wearable device 2 can e.g. be based on RFID (Radio Frequency Identification) or NFC (Near Field Communication). This will trigger the electronic lock to perform an access control procedure for the user identified by the wearable device 2. If the access control procedure is positive, the electronic lock will be set in an unlocked state, allowing the user to access the physical space. The same procedure can be used to set the electronic lock in a locked state. An access manager 7 is a computer which is used to allocate access to the user 1 as needed, to be able to open the electronic locks 22a-c. The wearable device 2 can communicate with the access manager, e.g. using a cellular network module within the wearable device 2 or via a smartphone connected with the wearable device 2 over a short range wireless link.

A usage scenario in the environment illustrated in FIG. 1 will now be described.

At the start of a shift, the user 1 reports to a logistics centre, at which the user is assigned a vehicle and a delivery schedule for the day. The user accepts by identifying him/herself using the wearable device.

Optionally, the vehicle can be started only after the user has provided identification on the wearable device.

Once the user arrives at a delivery location, the user exits the cabin and walks around to the back of the vehicle. The lock of the back door is opened by the user providing identification on the wearable device. Once the user has picked up the item to be delivered, e.g. a parcel, the user exits the vehicle and locks the back door by identifying using the wearable device.

Alternatively, an accelerometer in the vehicle is used to detect when the user has exited the vehicle, at which point the back door is locked. This detection can be based on an absence of movement or based on movement which differs from a movement pattern of the user. The movement pattern of the user has in that case been calibrated in advance, by the user moving about the cargo space in the vehicle for 3-6 minutes when in a calibration mode.

Alternatively, the back door is locked every time it is closed.

The wearable device can be used to improve security for the user. For instance, if the user is attacked and is forced on the ground, one or more accelerometers (see below) can detect this and send an alarm to a central office. Analogously, the wearable device can detect if the user falls down and does not get up again, e.g. for a health reason, at which point the wearable device sends an alarm.

Additional logic can be applied to enhance security. For instance, the wearable device may poll to require identification at regular intervals to indicate that the user is safe. This can be prompted by a small vibration of the wearable device which is only sensed by the user. Hence, every so often, the wearable device vibrates and the user provided identification, which is interpreted as the user being safe. If the user is kidnapped or under threat, the user can abstain from providing identification when prompted, which then triggers an alarm to be sent from the wearable device. The hours during which the polling of identification occurs can be based on working hours or awake hours.

If the user locks the back door using the wearable device, the cabin doors can be locked automatically.

Figure 2:
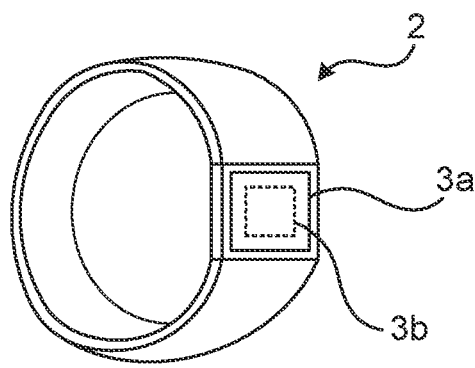
FIG. 2 is a schematic diagram illustrating an embodiment of a wearable device of FIG. 1.

FIG. 2 is a schematic diagram illustrating an embodiment of a wearable device 2 of FIG. 1 in the form of a wristband. The wearable device 2 comprises a first biometric sensor 3a for obtaining first biometric data and a second biometric sensor 3b for obtaining second biometric data. The second biometric sensor 3b captures second biometric data comprising a finger pressure parameter.

The wearable device 2 is configured to determine an identity of the user 1 based on the first biometric data and the second biometric data.

By measuring the finger pressure, an additional biometric parameter is captured which is difficult to copy and easy for the user to remember. The finger pressure parameter can be a curve of how the finger pressure varies over time, which improves the accuracy of identifying the user. The specific finger pressure pattern for the user needs to be captured initially, and may need to be periodically calibrated over time.

In this embodiment, the wearable device 2 is in the form of a wristband, to be worn around the wrist of the user.

The first biometric sensor 3a can comprise a fingerprint sensor. This allows for convenient identification of the user, e.g. by comparing a captured fingerprint with one or more templates. Optionally, the first biometric sensor 3a comprises a blood flow sensor. The blood flow sensor captures the blood flow, which varies over time in a user specific manner. Hence, the blood flow over time can be compared with blood flow templates to determine an identity of the user. Since the first biometric sensor 3a is used for finger pressure detection, the user needs to press the wearable device towards the body. This increases the quality of blood flow capturing. Optionally, the first biometric sensor 3a comprises a voice recognition unit. The spoken voice of a user is then captured using a microphone. The captured voice can be compared with voice templates to determine an identity of the user.

Optionally, the first biometric sensor 3a comprises an iris recognition unit. The iris of a user is then captured using a camera. The captured iris can be compared with iris templates to determine an identity of the user. The iris recognition unit can form part of the wearable device, or a rear vision camera of the vehicle can be used for this biometric sensor.

Optionally, the first biometric sensor 3a comprises a face recognition unit. The face of a user is then captured using a camera. The captured face can be compared with face templates to determine an identity of the user. The face recognition unit can form part of the wearable device, or a rear vision camera of the vehicle can be used for this biometric sensor.

The first biometric sensor 3a comprises an accelerometer, optionally combined with a gyro. The movement pattern of a user is then captured using the accelerometer and optionally the gyro. The captured movement patter can be compared with movement templates to determine an identity of the user.

Optionally, the first biometric sensor 3a comprises a breathalyser. Presence and/or extent of components of expired air of a user is then captured. The captured presence and/or extent of components can be compared with templates to determine an identity of the user.

Hence, the first biometric sensor 3a can comprise any suitable sensor for sensing a biometric of the user. Additional biometric sensors can be added to further improve accuracy of user identifications. More sensors imply reduces risk of false positive and false negative identifications.

Optionally, there is a sensor which detects if the wearable device 2 is removed from a users. This enables even greater reliability in determining which user carries the wearable device 2.

Figure 3:
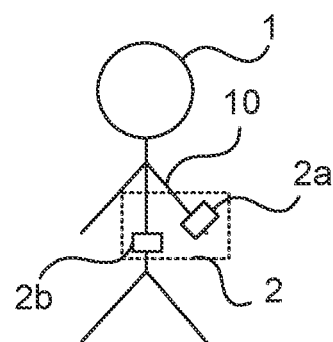
FIG. 3 is a schematic diagram illustrating an embodiment of a wearable device of FIG. 1 implemented using several sections.

FIG. 3 is a schematic diagram illustrating an embodiment of a wearable device 2 of FIG. 1 implemented using several sections 2a and 2b. In this embodiment, the wearable device 2 is made up by two separate sections, a first section 2a and a second section 2b. The sections 2a, 2b are separate but can communicate with each other using a wireless link, e.g. Bluetooth Low Energy (BLE), Bluetooth, etc.

The first section 2a can be in the form of the wristband of FIG. 2. The first section is attached to a limb 10 of the user, in this example an arm. The second section 2b can be attached to a body part of the user being distinct from the first limb 10 of the user. For instance, the second section 2b can be attached to a belt (and thus the torso of the user 1), a hat of the user, a shoe of the user, an ear of the user (as an ear clip), etc.

The second section 2b comprises a third biometric sensor 3c for obtaining third biometric data, wherein the wearable device 2 is configured to determine the identity of the user 1 based also on the third biometric data. When the first biometric 3a sensor is a first accelerometer, the third biometric sensor 3b can be a second accelerometer. Hence, the first accelerometer can be configured to measure acceleration of a part of a first limb 10 of the user 1 and the second accelerometer can be configured to measure acceleration of another body part of the user 1. The accelerometers can be triaxle accelerometers and optionally comprises respective gyros.

Figure 4:
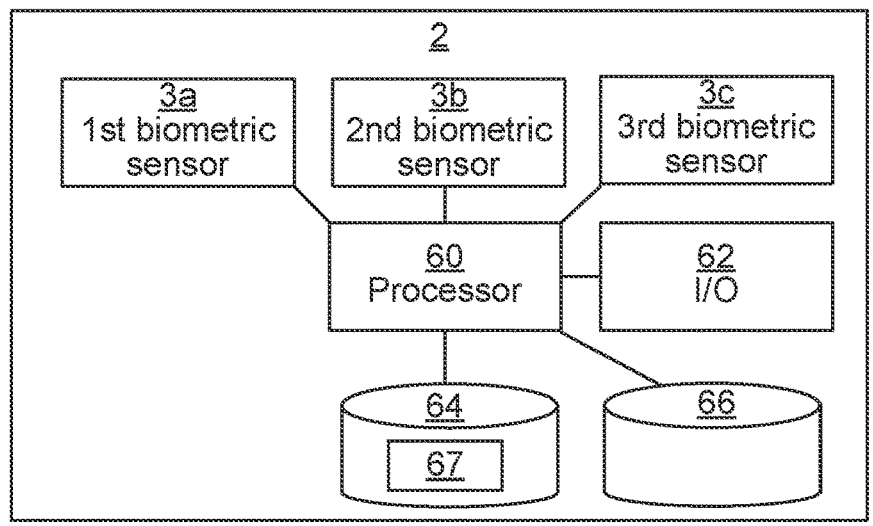
FIG. 4 is a schematic diagram illustrating components of the wearable device of FIG. 1.

By using two separate accelerometers on separate body parts of the user, the state of the user can be determined which much greater reliability. For instance, the respective accelerations can be double integrated to obtain a shift in position, which can e.g. be used to detect when the user 1 has fallen down or is otherwise in a horizontal position. In other words, by using multiple accelerometers on different body parts of the user, the wearable can detect movement with great accuracy and reliability. The detection of when a user has fallen down can also be made based on fast Fourier transform (FFT) of the acceleration signals from the two accelerometers and comparing with threshold values in one or more frequency components obtained through the FFT. When present, the gyro can also be of great help to identify the position of the user 1. FIG. 4 is a schematic diagram illustrating components of the wearable device 2 of FIG. 1. A processor 60 is provided using any combination of one or more of a suitable central processing unit (CPU), multiprocessor, microcontroller, digital signal processor (DSP), application specific integrated circuit etc., capable of executing software instructions 67 stored in a memory 64, which can thus be a computer program product. The processor 60 can be configured to execute the method described with reference to FIG. 5 below.

The memory 64 can be any combination of random access memory (RAM) and read only memory (ROM). The memory 64 also comprises persistent storage, which, for example, can be any single one or combination of magnetic memory, optical memory, solid-state memory, or even remotely mounted memory.

A data memory 66 is also provided for reading and/or storing data during execution of software instructions in the processor 60. The data memory 66 can be any combination of random access memory (RAM) and read only memory (ROM). The data memory 66 can e.g. comprise templates for biometric identification of a user.

The wearable device 2 further comprises an I/O interface 62 for communicating with other external entities. Optionally, the I/O interface 62 also includes a user interface.

A transceiver of the I/O interface 62 comprises suitable analogue and digital components to allow signal transmission and signal reception with a wireless device using one or more antennas. The transceiver can include a cellular module (using e.g. LTE (Long Term Evolution) or W-CDMA (wideband code division multiple access) for data access to the Internet.

Alternatively or additionally, the transceiver comprises a short-range communication module, e.g. BLE or Bluetooth for communication with a smartphone, to thereby gain data access to the Internet.

In FIG. 4, a first biometric sensor 3a, a second biometric sensor 3b and a third biometric sensor 3c are shown. Additional biometric sensors can be added to increase reliability of biometric identification of a user.

Other components of the wearable device 2 are omitted in order not to obscure the concepts presented herein.

It is to be noted that the wearable device 2 can be provided in two or more sections (see e.g. FIG. 3), in which case the different sections of the wearable device 2 can communicate with each other using a wireless link, e.g. BLE.

Figure 5:
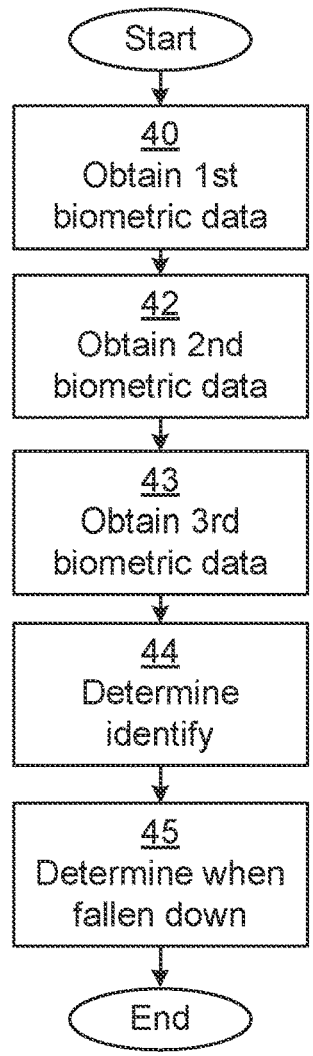
FIG. 5 is a flow chart illustrating a method for determining when a user has fallen down, performed in the wearable device of FIG. 1.

FIG. 5 is a flow chart illustrating a method for determining when a user has fallen down, performed in the wearable device of FIG. 1.

In an obtain first biometric data step 40, the wearable device obtains first biometric data of the user using a first biometric sensor of the wearable device. The first biometric sensor is a first accelerometer configured to measure acceleration of a part of a first limb of the user. Hence, the first biometric data is based on the acceleration of the first biometric sensor. In one embodiment, the first biometric data is the measured acceleration of the first biometric sensor.

In an obtain second biometric data step 42, the wearable device obtains second biometric data of the user using a second biometric sensor of the wearable device, the second biometric data comprising a finger pressure parameter.

In an obtain third biometric data step 43, the wearable device obtains third biometric data of the user using a third biometric sensor of the wearable device The third biometric sensor is a second accelerometer configured to measure acceleration of a body part of the user being distinct from the first limb of the user. Hence, the third biometric data is based on the acceleration of the third biometric sensor. In one embodiment, the third biometric data is the measured acceleration of the third biometric sensor.

In a determine identity step 44, the wearable device determines an identity of the user based on the first biometric data and the second biometric data. The identity is used to control access to a physical space, e.g. of the vehicle.

In a determine when fallen down step 45, the wearable device determines when the user has fallen down based on the first biometric data and the third biometric data.

The determining of when the user has fallen down can be based on double integrating acceleration data to determine a vertical movement difference between the first biometric sensor and the third biometric sensor. This is particularly useful when the vertical position differs significantly when standing up, e.g. if the first biometric sensor is on a wrist and the third biometric sensor is in a necklace. When the user has fallen down, the vertical position difference is much less than when the user is standing up.

The determining of when the user has fallen down can be based on performing a fast Fourier transform (FFT) of the accelerations detected by the first biometric sensor and the third biometric sensor. When a user falls down, the frequency components of the acceleration is significantly different from a deliberate motion, e.g. lying down on a sofa. This is exploited using the FFT processing.

The determining of when the user has fallen down is of great importance for the security of the user. The central control centre alerted of the fallen down user, allowing actions to be performed to ensure the security of the user. Additionally, when potential attackers learn that the fallen down detection is used, they will be less prone to follow through with plans to attack users. Using multiple biometric sensor to determine identity of the user gives an identification which is virtually impossible to spoof by an attacker. Moreover, there is a traceability on individual level, rather than based on a physical credential item such as a key card, fob, etc. The traceability on individual level provides a greater security and the recipient can trust the driver to a greater extent. In this way, drivers that may have had to wait for a specific person to receive the delivery may be given access to a building to drop off the delivery directly, making the delivery more efficient and thus saving time and cost.

Figure 6:
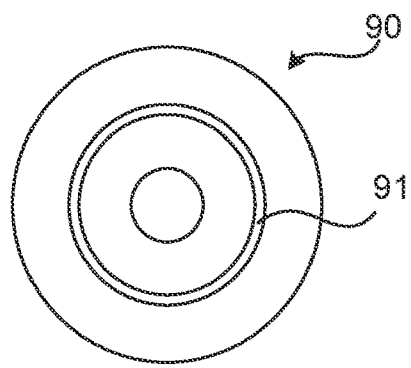
FIG. 6 shows one example of a computer program product comprising computer readable means.

FIG. 6 shows one example of a computer program product comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 4. While the computer program 91 is here schematically shown as a track on the depicted optical disk, the computer program can be stored in any way which is suitable for the computer program product, such as a removable solid state memory, e.g. a Universal Serial Bus (USB) drive.

Here now follows a list of embodiments from another perspective, enumerated with roman numerals.

i. A wearable device for identifying a user, the wearable device comprising:
   a first biometric sensor for obtaining first biometric data of the user; and
   a second biometric sensor for obtaining second biometric data of the user comprising a finger pressure parameter;
   wherein the wearable device is configured to determine an identity of the user is based on the first biometric data and the second biometric data, the identity being used to control access to a physical space.

ii. The wearable device according to embodiment i, wherein the first biometric sensor is a fingerprint sensor.

iii. The wearable device according to embodiment i, wherein the first biometric sensor is a blood flow sensor.

iv. The wearable device according to embodiment i or ii, further comprising a third biometric sensor for obtaining third biometric data, wherein the wearable device is configured to determine the identity of the user based also on the third biometric data.

v. The wearable device according to embodiment iv, wherein the first biometric sensor is a first accelerometer and the third biometric sensor is a second accelerometer.

vi. The wearable device according to embodiment v, wherein the first accelerometer is configured to measure acceleration of a part of a first limb of the user and the second accelerometer is configured to measure acceleration of a body part of the user being distinct from the first limb of the user.

vii. The wearable device according to any one of the preceding embodiments, wherein the first biometric sensor comprises a gyro.

viii. The wearable device according to any one of the preceding embodiments, wherein the physical space forms part of a vehicle.

ix. A method for identifying a user, the method being performed in a wearable device and comprising the steps of:
   obtaining first biometric data of the user using a first biometric sensor of the wearable device;
   obtaining second biometric data of the user using a second biometric sensor of the wearable device, the second biometric data comprising a finger pressure parameter; and
   determining an identity of the user based on the first biometric data and the second biometric data.

x. A computer program for identifying a user, the computer program comprising computer program code which, when run on a wearable device causes the wearable device to:

obtain first biometric data using a first biometric sensor of the wearable device;

obtain second biometric data using a second biometric sensor of the wearable device, the second biometric data comprising a finger pressure parameter; and determine an identity of the user based on the first biometric data and the second biometric data.

xi. A computer program product comprising a computer program according to embodiment x and a computer readable means on which the computer program is stored.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A wearable device for determining when a user has fallen down, the wearable device comprising:
 a first biometric sensor for obtaining first biometric data of the user, wherein the first biometric sensor is a first accelerometer configured to measure acceleration of a part of a first limb of the user; and
 an auxiliary biometric sensor for obtaining auxiliary biometric data, the auxiliary biometric sensor being a second accelerometer configured to measure acceleration of a body part of the user being distinct from the first limb of the user;
 a processor; and
 a memory storing instructions that, when executed by the processor, cause the wearable device to:
  determine when the user has fallen down based on the first biometric data and the auxiliary biometric data.

2. The wearable device according to claim 1, wherein the first biometric sensor comprises a fingerprint sensor.

3. The wearable device according to claim 1, wherein the first biometric sensor comprises a blood flow sensor.

4. The wearable device according to claim 1, wherein the instructions to determine when the user has fallen down comprise instructions that, when executed by the processor, cause the wearable device to: determine when the user has fallen down based on double integrating acceleration data to determine a vertical movement difference between the first biometric sensor and the auxiliary biometric sensor.

5. The wearable device according to claim 1, wherein the instructions to determine when the user has fallen down comprise instructions that, when executed by the processor, cause the wearable device to: determine when the user has fallen down based on performing a fast Fourier transform of the accelerations detected by the first biometric sensor and the auxiliary biometric sensor.

6. The wearable device according to claim 1, wherein the first biometric sensor comprises a gyro.

7. The wearable device according to claim 1, wherein at least one of the first biometric data or auxiliary biometric data are used to control access to a physical space, and wherein the physical space forms part of a vehicle.

8. The wearable device according to claim 1, further comprising instructions that, when executed by the processor, cause the wearable device to:
 send an alarm indicating that the user has fallen down.

9. A method for determining when a user has fallen down, the method being performed in a wearable device and comprising:
 obtaining first biometric data of the user using a first biometric sensor of the wearable device, wherein the first biometric sensor is a first accelerometer configured to measure acceleration of a part of a first limb of the user;
 obtaining auxiliary biometric data of the user using an auxiliary biometric sensor of the wearable device, wherein the auxiliary biometric sensor is a second accelerometer configured to measure acceleration of a body part of the user being distinct from the first limb of the user; and
 determining when the user has fallen down based on the first biometric data and the auxiliary biometric data.

10. The method according to claim 9, wherein the determining when the user has fallen down comprises determining when the user has fallen down based on double integrating acceleration data to determine a vertical movement difference between the first biometric sensor and the auxiliary biometric sensor.

11. The method according to claim 9, wherein the determining when the user has fallen down comprises determining when the user has fallen down based on performing a fast Fourier transform of the accelerations detected by the first biometric sensor and the auxiliary biometric sensor.

12. The method according to claim 9, further comprising:
 sending an alarm indicating that the user has fallen down.

13. A non-transitory computer readable medium storing a computer program for determining when a user has fallen down, the computer program comprising computer program code which, when run on a wearable device, causes the wearable device to:
 obtain first biometric data using a first biometric sensor of the wearable device, wherein the first biometric sensor is a first accelerometer configured to measure acceleration of a part of a first limb of the user;
 obtain auxiliary biometric data of the user using an auxiliary biometric sensor of the wearable device, wherein the auxiliary biometric sensor is a second accelerometer configured to measure acceleration of a body part of the user being distinct from the first limb of the user; and
 determine when the user has fallen down based on the first biometric data and the auxiliary biometric data.

* * * * *